(12) United States Patent
Kay et al.

(10) Patent No.: US 11,473,080 B2
(45) Date of Patent: Oct. 18, 2022

(54) METHOD FOR GENERATING HIGH AFFINITY, BIVALENT BINDING AGENTS FOR SANDWICH ASSAYS

(71) Applicant: The Board of Trustees of the University of Illinois, Urbana, IL (US)

(72) Inventors: Brian K. Kay, Chicago, IL (US);
Kevin T. Gorman, Chicago, IL (US);
Renhua Huang, Rockville, MD (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 603 days.

(21) Appl. No.: 16/180,290

(22) Filed: Nov. 5, 2018

(65) Prior Publication Data

US 2019/0055547 A1 Feb. 21, 2019

Related U.S. Application Data

(63) Continuation-in-part of application No. 14/698,158, filed on Apr. 28, 2015, now abandoned.

(60) Provisional application No. 61/986,192, filed on Apr. 30, 2014.

(51) Int. Cl.
| | |
|---|---|
| *C12N 15/10* | (2006.01) |
| *C07K 16/00* | (2006.01) |
| *C07K 16/40* | (2006.01) |
| *C12N 15/86* | (2006.01) |

(52) U.S. Cl.
CPC ........ *C12N 15/1037* (2013.01); *C07K 16/005* (2013.01); *C07K 16/40* (2013.01); *C12N 15/1058* (2013.01); *C12N 15/86* (2013.01); *C07K 2317/31* (2013.01); *C07K 2317/92* (2013.01); *C07K 2318/20* (2013.01); *C12N 2795/14143* (2013.01)

(58) Field of Classification Search
None
See application file for complete search history.

(56) References Cited

U.S. PATENT DOCUMENTS

| | | | |
|---|---|---|---|
| 8,685,893 B2 | 4/2014 | Sidhu et al. | 506/14 |
| 2004/0023207 A1 | 2/2004 | Polansky | 435/5 |
| 2005/0048512 A1 | 3/2005 | Kolkman et al. | 435/6.1 |
| 2011/0059076 A1* | 3/2011 | McDonagh | C07K 16/32 |
| | | | 424/133.1 |
| 2011/0143963 A1 | 6/2011 | Koide et al. | 506/18 |
| 2011/0318269 A1 | 12/2011 | Reiersen et al. | 424/9.1 |
| 2013/0045507 A1 | 2/2013 | Huovinen et al. | 435/91.2 |
| 2015/0315566 A1* | 11/2015 | Kay | C07K 16/40 |
| | | | 506/1 |
| 2016/0032280 A1 | 2/2016 | Weiner et al. | 530/387.1 |
| 2016/0039940 A1 | 2/2016 | Andersen et al. | 424/139.1 |
| 2016/0130347 A1 | 5/2016 | Bruenker et al. | 424/136.1 |

OTHER PUBLICATIONS

Gorman et al. Tandem phage-display for the identification of non-overlapping binding pairs of recombinant affinity reagents. Nucleic Acids Research 45(18):e158 (9 pages). (Year: 2017).*

(Continued)

*Primary Examiner* — Samuel C Woolwine
(74) *Attorney, Agent, or Firm* — Licata & Tyrrell P.C.

(57) ABSTRACT

A combined Kunkel mutagenesis and phage-display method for producing bivalent binding agents is provided.

15 Claims, 4 Drawing Sheets

Specification includes a Sequence Listing.

(56) References Cited

OTHER PUBLICATIONS

Blomberg et al. Terbium and Rhodamine as Labels in a Homogeneous Time-resolved Fluorometric Energy Transfer Assay of the β Subunit of Human Chorionic Gonadotropin in Serum. Clinical Chemistry 45(6): 855-861. (Year: 1999).*
Gorman, K. Designer Affinity Reagents for Biomarker Detection. Thesis, University of Illinois—Chicago (130 pages). (Year: 2017).*
Information regarding publication date of Gorman Thesis [online] [retrieved on Sep. 13, 2020] retrieved from: https://indigo.uic.edu/articles/Designer_Affinity_Reagents_for_Biomarker_Detection/10840940 (Year: 2020).*
Voller et al. (Journal of Clinical Immunopathology 31:507-520. (Year: 1978).*
Huber et al. In vitro selection and characterization of DARPins and Fab fragments for the co-crystalization of membrane proteins: The Na+-citrate symporter CitS as an example. Journal of Structural Biology 159:206-221. (Year: 2007).*
Abdiche et al. "Exploring Blocking Assays Using Octet, ProteOn, and Biacore Biosensors" Analytical Biochemistry 2009 386:172-180.
Brammer et al. "A Target-Unrelated Peptide in an M13 Phage Display Library Traced to an Advantageous Mutation in the Gene II Ribosome-Binding Site" Analytical Biochemistry 2008 373:88-98.
Daugherty et al. "Quantitative Analysis of the Effect of the Mutation Frequency on the Affinity Maturation of Single Chain Fv Antibodies" Proceedings of the National Academy of Sciences 2000 97(5):2029-2034.
Drow et al. "Indirect Sandwich Enzyme-Linked Immunosorbent Assay for Rapid Detection of *Haemophilus influenza* Type b Infection" Journal of Clinical Microbiology 1979 10(4):442-450.
Fagéte et al. "Specificity Tuning of Antibody Fragments to Neutralize Two Human Chemokines with a Single Agent" mAbs 2009 1(3):288-296.
Fellouse et al. "High-Throughput Generation of Synthetic Antibodies from Highly Functional Minimalist Phage-Displayed Libraries" Journal of Molecular Biology 2007 373:924-940.
Gram et al. "In vitro Selection and Affinity Maturation of Antibodies from a Naïve Combinatorial Immunoglobulin Library" Proceedings of the National Academy of Sciences USA 1992 89:3576-3580.
Groves et al. "Affinity Maturation of Phage Display Antibody Populations Using Ribosome Display" Journal of Immunological Methods 2006 313:129-139.
Huang et al. "Isolation of Monobodies that Bind Specifically to the SH3 Domain of the Fyn Tyrosine Protein Kinase" New Biotechnology 2012 29(5):526-533.
Jäger et al. "High Level Transient Production of Recombinant Antibodies and Antibody Fusion Proteins in HEK293 Cells" BMC Biotechnology 2013 13:52.
Kunkel, T. A. "Rapid and Efficient Site-Specific Mutagenesis Without Phenotypic Selection" Proceedings of the National Academy of Sciences USA 1985 82:488-492.
Kunkel et al. "Rapid and Efficient Site-Specific Mutagenesis Without Phenotypic Selection" Methods in Enzymology 1987 154:367-382.
Lee et al. "Bivalent Antibody Phage Display Mimics Natural Immunoglobulin" Journal of Immunological Methods 2004 284:119-132.
Ling, M. M. "Large Antibody Display Libraries for Isolation of High-Affinity Antibodies" Combinatorial Chemistry & High Throughput Screening 2003 6:421-432.
Menendez, A. and Scott, J. K. "The Nature of Target—Unrelated Peptides Recovered in the Screening of Phage-Displayed Random Peptide Libraries with Antibodies" Analytical Biochemistry 2005 336:145-157.
Scholle et al. "Efficient Construction of a Large Collection of Phage-Displayed Combinatorial Peptide Libraries" Combinatorial Chemistry & High Throughput Screening 2005 8:545-551.
Silverman et al. "Multivalent Avimer Proteins Evolved by Exon Shuffling of a Family of Human Receptor Domains" Nature Biotechnology 2005 23(12):1556-1561.
Sugimoto et al. "A Simple and Efficient Method for the Oligonucleotide-Directed Mutagenesis Using Plasmid Dna Template and Phosphorothioate-Modified Nucleotide" Analytical Biochemistry 1989 179:309-311.
Tonikian et al. "Identifying Specificity Profiles for Peptide Recognition Modules from Phage-Displayed Peptide Libraries" Nature Protocols 2007 2(6):1368-1386.
Vandeyar et al. "A Simple and Rapid Method for the Selection of Oligodeoxynucleotide-Directed Mutants" Gene 1988 65:129-133.
Wells, J. A. and Estell, D. A. "Subtilisin—an Enzyme Designed to be Engineered" Trends in Biochemical Science 13(8):291-297 (1988).
Wojcik et al. "A Potent and Highly Specific FN3 Monobody Inhibitor of the Abl SH2 Domain" Nature Structural & Molecular Biology 17(4):519-527 (2010).
Yang et al. "CDR Walking Mutagenesis for the Affinity Maturation of a Potent Human Anti-HIV-1 Antibody into the Picomolar Range" Journal of Molecular Biology 1995 254:392-403.
Zhang et al. "Seamless Ligation Cloning Extract (SLiCE) Cloning Method" Methods in Molecular Biology 2014 1116:235-244.
Ahmad et al. "scFv Antibody: Principles and Clinical Application" Clinical and Developmental Immunology 2012 pp. 1-15.
Koide et al. "The fibronectin Type III Domain as a Scaffold for Novel Binding Proteins" J. Mol. Biol. 1998 284:1141-1151.
Office communication dated May 19, 2017 from U.S. Appl. No. 14/698,158, filed Apr. 28, 2015.
Office communication dated Nov. 1, 2017 from U.S. Appl. No. 14/698,158, filed Apr. 28, 2015.

* cited by examiner

```
agcgtttagc gcatcggcgg acgtcgtcga gcagaaattg atcagcgagg aggatctgat ggccgtttct gatgttccgc
                                    E  Q  K  L  I  S  E  E  D  L  M  A  V  S  D  V  P
                                    |_____MYC TAG_____|  |__FN3 I gtaagctgga agttgttgct gcgaccccga ctagcctgct gatcagctgg gatgctcctt aatgaaggcc tctttattac
 R  K  L  E  V  V  A  A  T  P  T  S  L  L  I  S  W  D  A  P  -  -  R  P  L  Y  Y
_____FN3 I_____ cgtatcacgt acggtgaaac cggtggtaac tcccccggttc aggagttcac tgtacctggt tccaagtcta ctgctaccat
 R  I  T  Y  G  E  T  G  G  N  S  P  V  Q  E  F  T  V  P  G  S  K  S  T  A  T  I
_____FN3 I_____ cagcggcctg aaaccgggtg ttgactatac catcactgta tacgctgtta cttaatgaag gccttatagc aagccaatct
 S  G  L  K  P  G  V  D  Y  T  I  T  V  Y  A  V  T  -  -  R  P  Y  S  K  P  I
_____FN3 I_____ cgattaacta ccgtaccagc ggaggggag gttctggagg cggtgggtct ggtggtggcg gctctggagg cggtggtagc
 S  I  N  Y  R  T  S  G  G  G  G  S  G  G  G  G  S  G  G  G  G  S
_____FN3 I_____  |_____LINKER_____ ggaggcggag gttctgatta caaggacgac gatgacaagc ttgctagcgc catggccgtt tctgatgttc cgcgtaagct
 G  G  G  G  S  D  Y  K  D  D  D  D  K  L  A  S  A  M  A  V  S  D  V  P  R  K  L
_____  |____FLAG TAG____|                         |_____FN3 II_____ ggaagttgtt gctgcgaccc cgactagcct gctgatcagc tgggatgctc cttacttaatg aaggcctttat taccgtatca
 E  V  V  A  A  T  P  T  S  L  L  I  S  W  D  A  P  -  -  R  P  L  Y  Y  R  I
_____FN3 II_____ cgtacggtga aaccggtggt aactcccccgg ttcaggagt cactgtacct ggttccaagt ctactgctac catcagcggc
 T  Y  G  E  T  G  G  N  S  P  V  Q  E  F  T  V  P  G  S  K  S  T  A  T  I  S  G
_____FN3 II_____ ctgaaaccgg gtgttgacta taccatcact gtatacgctg ttacttaatg aaggccttat agcaagccaa tctcgattaa
 L  K  P  G  V  D  Y  T  I  T  V  Y  A  V  T  -  -  R  P  Y  S  K  P  I  S  I  N
_____FN3 II_____ ctaccgtacc agcggccgcg tcgacgggcg cgccaattg atcgacccat tcgtttctga atatcaaggc caatcgtctg
 Y  R  T  S
____FN3 II
```

FIG. 3

METHOD FOR GENERATING HIGH AFFINITY, BIVALENT BINDING AGENTS FOR SANDWICH ASSAYS

INTRODUCTION

This application is a continuation-in-part application of U.S. Ser. No. 14/698,158, filed Apr. 28, 2015, which claims the benefit of priority of U.S. Provisional Application No. 61/986,192, filed Apr. 30, 2014, the contents of which are incorporated herein by reference in their entireties.

This invention was made with government support under contract number DK093444 awarded by the National Institutes of Health. The government has certain rights in the invention.

BACKGROUND

In the field of antibody engineering, it is often desirable to generate bivalent affinity reagents because of their useful properties including impressive binding affinity and use in sandwich ELISA (Silverman, et al. (2005) *Nat. Biotechnol.* 23:1556-61; Lee, et al. (2004) *J. Immunol. Meth.* 284:119-132; Drow, et al. (1979) *J. Clin. Microbiol.* 10:9). The traditional approach for isolating a pair of binders to non-overlapping epitopes (on the target protein) has been laborious. One must perform affinity selection, additional mutagenesis, further affinity selection, and finally epitope binning to find binding pairs that interact with different epitopes (Abdiche, et al. (2009) *Anal. Biochem.* 386:172-80). In addition to being time consuming, this approach is also not amenable to high-throughput strategies and is therefore not cost effective.

Several techniques are available for preparing antibody variants via site-directed mutagenesis. Cassette mutagenesis (Wells & Estell (1988) *Trends Biochem. Sci.* 13:291-297), which requires restriction enzyme digestion and ligation to incorporate mutagenic sequences, has been supplanted by the QUIKCHANGE method (Vandeyar, et al. (1988) *Gene* 65:129-133; Sugimoto, et al. (1989) *Anal. Biochem.* 179:309-11). In QUIKCHANGE, a pair of complementary oligonucleotides, containing the desired mutation(s), is used to amplify the entire plasmid with a high-fidelity polymerase, followed by DpnI digestion to remove the parental strand. A third widely used technique is Kunkel mutagenesis (Kunkel (1985) *Proc. Natl. Acad. Sci. USA* 82:488-92; Kunkel, et al. (1987) *Methods Enzymol.* 154:367-382; Scholle, et al. (2005) *Comb. Chem. High Throughput Screen.* 8:545-551; Tonikian, et al. (2007) *Nature Protocols* 2:1368-1386; Wojcik, et al. (2010) *Nature Struct. Mol. Biol.* 17:519-527) and derivatives thereof (See US 2013/0045507), where uracil-inserted, circular, single-stranded DNA (ssDNA) is used as a template to synthesize double-stranded DNA (dsDNA) in vitro with a short oligonucleotide primer that introduces a mutation. After dsDNA is introduced into bacteria, recombinant clones predominate due to cleavage of the uracilated strand in vivo. Kunkel mutagenesis has been useful in phage-display experiments that are based on M13 or related phage, as the viral particles contain a circular, single-stranded genome (Scholle, et al. (2005) *Comb. Chem. High Throughput Screen.* 8:545-551; Fellouse, et al. (2007) *J. Mol. Biol.* 373:924-9401; Huang et al. (2012) *N. Biotechnol.* 29(5):526-33; U.S. Pat. No. 8,685,893).

As the number of the theoretical permutations in a protein engineering experiment can be astronomical, it is desirable to construct phage-displayed libraries that include a vast number of mutants, as it has been observed that the size of a phage library is closely correlated with the affinity of the isolated mutants (Ling (2003) *Comb. Chem. High Throughput Screen.* 6:421-432). While the size of the library is a limiting factor in isolating desired clones, the quality of the phage library (i.e., the percentage of the phage particles displaying the recombinant polypeptides out of the total phage pool), also significantly influences the efficiency and the outcome of affinity selections. For example, some studies have found that non-recombinant clones, or target-unrelated clones, can overwhelm the target-binding clones in the library due to the advantages associated with steps of phage propagation or affinity selection (Menendez & Scott (2005) *Anal. Biochem.* 336:145-157; Brammer, et al. (2008) *Anal. Biochem.* 373:88-98).

Even with improvements in the size and quality of a phage-displayed library, affinity maturation experiments are usually necessary to fine-tune binders for improved specificity (Huang et al. (2012) *N. Biotechnol.* 29(5):526-33; Fagete, et al. (2009) *MAbs.* 1:288-296), affinity (Huang et al. (2012) *N. Biotechnol.* 29(5):526-33; Yang, et al. (1995) *J. Mol. Biol.* 254:392-403; Groves, et al. (2006) *J. Immunol. Methods* 313:129-139), or both (Huang et al. (2012) *N. Biotechnol.* 29(5):526-33). One simple method is to generate secondary (i.e., mutant) libraries through an error-prone polymerase chain reaction (PCR) (Gram, et al. (1992) *Proc. Natl. Acad. Sci. USA* 89:3576-3580; Daugherty, et al. (2000) *Proc. Natl. Acad. Sci. USA* 97:2029-2034), and repeat the affinity selections under more stringent conditions (i.e., less target, longer wash times, more washes). Nevertheless, generating each secondary library can be time-consuming, and unless large, may be inadequate for isolating mutants with dramatically improved properties.

Alternative approaches for generating bivalent molecules having a high affinity and specificity for a given target have been described. For example, US 2011/0143963 describes affinity reagents, termed "modular molecular affinity clamps," that have a clamp-like or clamshell architecture and are composed of two discrete modules, each of which bind the same target peptide motif. Further, Jager, et al. ((2013) *BMC Biotechnol.* 13:52) describe scFv-Fc antibody fusion proteins, which can be transiently expressed and screened in a high-throughput recombinant manner. Moreover, US 2005/048512 describes affinity clamps, which are designed to bind two sides of the same epitope, for use in therapeutic applications.

SUMMARY OF THE INVENTION

This invention is a method for generating a high affinity, bivalent binding agent for a sandwich assay by (a) amplifying a first and second library of nucleic acids, each library encoding a population of binding agents that bind to different epitopes on a target molecule, to generate a first and second pool of megaprimers; (b) annealing the first and second pool of megaprimers of (b) to a single-stranded, uracilated phage-display vector comprising a first binding agent coding region and second binding agent coding region each capable of hybridizing to the first or second pool of megaprimers, wherein the first and second binding agent coding regions are in tandem and linked via a linker; (c) primer extending the first and second pool of megaprimers of (b) to generate a phage-display library of bivalent phage clones; (d) screening the phage-display library to identify a bivalent binding agent comprising first and second binding agents, each of which binds to a different epitope on the target molecule; and (e) conjugating each of the first and second binding agents to a member of a sandwich assay, e.g., a solid support member and reporter member of a heterogenous or a donor member and acceptor member of a homogeneous sandwich assay. In some embodiments the population of binding agents includes a library of antibody fragments, single-domain antibodies, Forkhead-Associated domains, monobodies, minibodies, single-chain variable fragments, AFFIBODY molecules, affilins, anticalins, designed ankyrin repeat proteins, nanofitins, linear peptides or a combination thereof. In other embodiments, step (d) of the method further includes (i) amplifying nucleic acid encoding the first and second binding agents to generate megaprimers; (ii) annealing the megaprimers of (i) to a library of single-stranded phage-display vectors comprising a randomized library of linkers so that the first and second binding agent coding regions are in tandem and linked via a member of the randomized library of linkers; (iii) primer extending the megaprimers of (ii) to generate a phage-display library of bivalent phage clones; and (iv) screening the phage-display library to identify a bivalent binding agent that binds to different epitopes on the target molecule. In certain embodiments, linkers of the randomized library of linkers may include rigid linkers, flexible linkers, cleavable linkers, or a combination thereof, wherein the flexible linkers may optionally include at least one calmodulin binding peptide. A kit containing the first and second binding agents generated by the method of this invention is also provided, wherein said first and second binding agents are linked or separated.

BRIEF DESCRIPTION OF THE DRAWINGS

FIG. 3 shows the nucleotide (SEQ ID NO:16) and deduced amino acid sequence (SEQ ID NOs:17-20) of a portion of a phage-display vector encoding tandem FN3 proteins. Stop codons (TAA and TGA) and StuI restriction sites introduced into each BC and FG loop region of the FN3 coding sequences are indicated. Myc and FLAG® (DYKDDDDK) tags and linker sequences are also indicated.

DETAILED DESCRIPTION OF THE INVENTION

Figure 1:
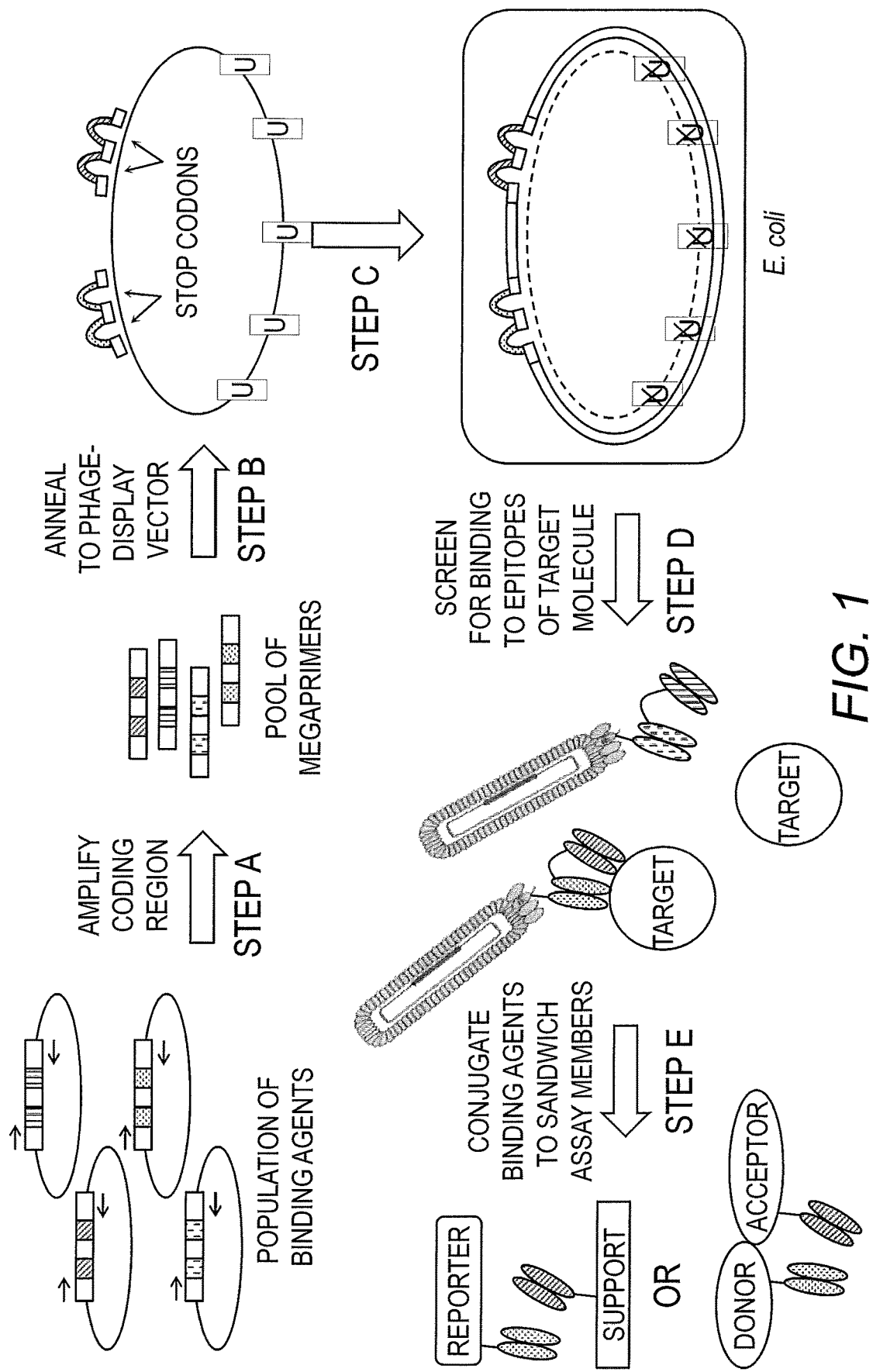
FIG. 1 depicts the inventive method of megaprimer shuffling for tandem affinity reagents (MegaSTAR). Megaprimers are created by PCR amplification of the coding region for a pool of pre-selected clones (Step A). The megaprimers are then annealed to single-stranded, uracilated tandem DNA templates containing two coding regions (Step B) linked via a linker. The recombinant strands are then filled in via DNA polymerase and transformed into *E. coli*. The bacteria then degrade the uracilated parent strand, leaving the recombinant strands that now allow the phage to display tandem, linked binders (Steps C and D). When performed with a population of clones, this creates a new "bivalent library" of use in subsequent affinity selection to isolate bivalent reagents with the strongest affinity for the target. One or both of the binding agents of the bivalent molecule are then conjugated to a member of a heterogenous sandwich assay, i.e., a reporter member and solid support member; or a member of a homogenous sandwich assay, i.e., an acceptor member or donor member (Step E).

It has now been shown that Kunkel mutagenesis and phage-display can be combined to generate high affinity bivalent binding agents. The resulting binding agents are unique in that they simultaneously bind to two distinct epitopes on the same target protein. The present method allows for the rapid and efficient generation of these binding agents in a high throughput manner to any target of interest and are of particular use in the generation of binding agents for sandwich assays. This invention converts the output of an affinity selection to a bivalent display format via a technology referred to herein as Megaprimer Shuffling for Tandem Affinity Reagents (MegaSTAR). This method relies on synthesizing a "bivalent library" by first generating a pool of megaprimers from a selection output, and annealing them randomly to a bivalent vector. This new "bivalent library" is then used for further affinity selection to identify tandem reagents with the highest affinity for a target molecule. This allows for the concurrent examination of many different combinations of binding agents, thereby eliminating the need for pair-wise clonal analysis. Ultimately, this method greatly decreases the time and cost of creating bivalent binding agents of use in diagnostic and laboratory applications.

Accordingly, the present invention is a method for generating a high affinity, bivalent binding agent for a sandwich assay by (a) amplifying a first and second library of nucleic acids, each library encoding a population of binding agents that bind to different epitopes on a target molecule, to generate a first and second pool of megaprimers; (b) annealing the first and second pool of megaprimers of (b) to a single-stranded, uracilated phage-display vector comprising a first binding agent coding region and second binding agent coding region each capable of hybridizing to the first or second pool of megaprimers, wherein the first and second binding agent coding regions are in tandem and linked via nucleic acids encoding a linker; (c) primer extending the first and second pool of megaprimers of (b) to generate a phage-display library of bivalent phage clones; (d) screening the phage-display library to identify a bivalent binding agent comprising a first binding agent and second binding agent, each of which binds to a different epitope on the target molecule; and (e) conjugating each of the first and second binding agents to a member of a sandwich assay. See the illustrative example of the instant method depicted in FIG. 1.

For the purposes of the present invention, a "binding agent" refers to a protein that has a high affinity for, and specifically binds to, a target molecule, e.g., an antigen. A "bivalent binding agent" refers to a molecule composed of two binding agents, each of which binds to a different epitope. In some embodiments, the epitopes are present on the same antigen or target molecule of interest. In other embodiments, the epitopes are present on two different antigens or target molecules of interest.

As used herein, the term "affinity" refers to the non-random interaction of two molecules. Affinity, or the strength of the interaction, can be expressed quantitatively as a dissociation constant ($K_D$). Binding affinity can be determined using standard techniques. In particular embodiments, the binding agents of this invention have a high affinity for a target molecule, with $K_D$s in the range of low µM (e.g., 1-10 µM) to nM, or more preferably in the range of nM to µM.

Binding agents in accordance with this invention are artificial proteins that are composed of fragments of antibodies (e.g., Fab and Fd fragments), single-domain antibodies, Forkhead-Associated (FHA) domains, monobodies, minibodies, single-chain variable fragments (scFv), AFFIBODY molecules, affilins, anticalins, DARPins (i.e., designed ankyrin repeat proteins), and nanofitins (also known as affitins). Other binding agents that can be generated using this method include receptors, enzymes, peptides and protein ligands. In certain embodiments, the binding agent is a single chain molecule and/or monomeric molecule. Desirably, the binding agent of the invention is in the range of 5 to 800 amino acid residues in length, or more desirably 60 to 600 amino acid residues in length. Moreover, the binding agent is preferably thermal stable, lacks cysteine residues, can be expressed via a recombinant expression system (e.g., E. coli), has a known three-dimensional structure, has uniform biochemical properties among variants, does not bind metal ions, and/or can bind to one or more target molecules.

Single-domain antibodies or nanobodies are fragments composed of a single monomeric variable antibody domain (Harmsen & De Haard (2007) Appl. Microbiol. Biotechnol. 77:13-22). Like a whole antibody, it is able to bind selectively to a specific antigen. Single-domain antibodies are typically ~110 amino acid residues long and can be derived from heavy-chain antibodies found in camelids (i.e., $V_HH$ fragments) or cartilaginous fish (i.e., $V_{NAR}$). An alternative approach is to split the dimeric variable domains from common IgG from humans or mice into monomers (Holt, et al. (2003) Trends Biotechnol. 21:484-490). As with antibodies, the CDRs of nanobodies can be modified to alter the specificity of the nanobodies.

The Forkhead-Associated domain is a phosphopeptide recognition domain found in many regulatory proteins (Hofmann & Buchner (1995) Trends Biochem. Sci. 20:347-9). FHA domains are approximately 65-100 amino acid residues and display specificity for phosphothreonine-containing epitopes, but can also recognize phosphotyrosine with relatively high affinity. The FHA domain forms an 11-stranded β-sandwich that has a short α-helix inserted between β strands 2 and 3 and an α-helical region at the extreme C-terminus. The peptide binding site is created by the loop regions between β 3/4, β 4/5, and β 6/7 (Durocher, et al. (2000) Mol. Cell 6:1169-1182), which can be modified to alter specificity and affinity.

Monobodies, also known as Adnectins, are 94 amino acid proteins, which are based upon the structure of human fibronectin, in particular the tenth extracellular type III domain of fibronectin. This domain, referred to as the FN3 scaffold, has a structure similar to antibody variable domains, with two β-sheets, one constituted by β-strands A, B and E, and the other by β-strands C, D, F and G (Koide & Koide (2007) Methods Mol. Biol. 352:95-109). The specificity of monobodies can be tailored by modifying the loops BC (between the second and third beta sheets) and FG (between the sixth and seventh sheets) (Koide, et al. (1998) J. Mol. Biol. 284:1141-51). An exemplary FN3 monobody scaffold has the amino acid sequence:

```
                                          (SEQ ID NO: 1)
VSDVPRDLEV VAATPTSLLI SWDAPAVTVR YYRITYGETG
GNSPVQEFTV PGSKSTATIS GLKPGVDYTI TVYAVTGRGD
SPASSKPISI NYRT.
```

See U.S. Pat. No. 6,818,418. Another exemplary FN3 monobody scaffold includes the sequence:

```
                                          (SEQ ID NO: 2)
MAVSDVPRKL EVVAATPTSL LISWDAPCRK CLYYRITYGE
TGGNSPVQEF TVPGSKSTAT ISGLKPGVDY TITVYAVTRL
EFISKPIISI NYRI.
```

A minibody scaffold, which is related to the immunoglobulin fold, is a protein generated by deleting three beta strands from a heavy chain variable domain of a monoclonal antibody (Tramontano, et al. (1994) J. Mol. Recognit. 7:9). This protein includes 61 residues and can be used to present two hypervariable loops. In some embodiments, a minibody is a homodimer, wherein each monomer is a single-chain variable fragment (scFv) linked to a human IgG1 CH3 domain by a linker, such as a hinge sequence.

Single-chain variable fragments (scFv) are fusion proteins composed of the variable regions of the heavy ($V_H$) and light ($V_L$) chains of immunoglobulins, which are connected by a short peptide of ten to about 25 amino acid residues. The peptide is usually rich in glycine for flexibility, as well as serine or threonine for solubility, and can either connect the N-terminus of the $V_H$ with the C-terminus of the $V_L$, or vice versa. As with antibodies, the CDRs of scFv molecules can be modified to alter the specificity of the scFv.

Affibody molecules are small proteins (e.g., 58 amino acid residues) with a three-helix bundle domain, originally based upon the Z domain of staphylococcal protein A (Ståhl & Nygren (1997) Pathol. Biol. (Paris) 45:66-76; Nilsson, et al. (1987) Prot. Eng. 1:107-133; and U.S. Pat. No. 5,143,844). Based on the Z protein as a basic structure or scaffold, mutagenesis of surface-exposed amino acids can be carried out to create variants with an altered binding affinity. See, U.S. Pat. No. 6,534,628; Nord, et al. (1995) Prot. Eng. 8:601-608; Nord, et al. (1997) Nat. Biotech. 15:772-777.

Affilins are proteins that are structurally derived from human gamma-B crystallin or ubiquitin. The binding region of affilins is located in a beta sheet (Ebersbach, et al. (2007) J. Mol. Biol. 372:172-185; Vijay-Kumar, et al. (1987) J. Mol. Biol. 194:531-44), such that modification of near-surface amino acid residues of these proteins alters specificity. In particular, the near surface amino acids 2, 4, 6, 15, 17, 19, 36 and 38 of gamma crystalline are typically modified (see, WO 01/04144), whereas residues 2, 4, 6, 62, 63, 64, 65 and 66 of ubiquitin are typically modified (see, WO 2006/040129).

Anticalins are artificial proteins derived from lipocalins, which can bind to either proteins or small molecules (Weiss & Lowman (2000) Chem. Biol. 7:547-554). Lipocalins of use in this invention include, but are not limited to the bilin-binding protein (BBP) from Pieris brassicae (Beste, et al. (1999) Proc. Natl. Acad. Sci. USA 96:1898-1903; Schmidt & Skerra (1994) Eur. J. Biochem. 219:855-863; Schlehuber, et al. (2000) J. Mol. Biol. 297:1105-1120) and bovine retinol-binding protein (RBP) (Berni, et al. (1990) Eur. J. Biochem. 192:507-513). Anticalins have a barrel structure formed by eight antiparallel β-strands pairwise connected by loops. Sixteen 16 amino acid residues, distributed across the four loops, form the binding site, which can be mutagenized to modify affinity and selectivity (Skerra (2008) FEBS J. 275:2677-83).

DARPins derived from ankyrin proteins are composed of at least three, usually four or five repeat motifs, and have a molecular mass of about 14 to 18 kDa. Using a combination of sequence and structure consensus analyses, a amino acid residue ankyrin repeat module with seven randomized positions has been developed as a binding agent (Binz, et al. (2003) *J. Mol. Biol.* 332:489-503).

Nanofitins are 66 amino acid residue proteins derived from the DNA binding protein Sac7d of *Sulfolobus acidocaldarius* (EP 2469278). The binding area of nanofitins is located on the surface and is composed of 14 residues (i.e., residues 7-9, 21, 22, 24, 26, 29, 31, 33, 40, 42, 44, and 46), which can be modified to alter specificity (Mouratou, et al. (2007) *Proc. Natl. Acad. Sci. USA* 104:17983-8).

In accordance with the method of the invention, a first library and second library of nucleic acids, each library encoding a population of binding agents that bind to different epitopes on a target molecule, are amplified to generate a first pool and second pool of megaprimers (See FIG. 1, Step A). Each of the first and second library of nucleic acids encodes a single type of binding agent, e.g., antibody fragments, single-domain antibodies, FHA domains, monobodies, minibodies, scFv, AFFIBODY molecules, affilins, anticalins, DARPins or nanofitins. By way of illustration, the first library of nucleic acids encodes monobodies and the second library of nucleic acids encodes DARPins; the first library of nucleic acids encodes monobodies and the second library of nucleic acids encodes AFFIBODY molecules; the first library of nucleic acids encodes single-domain antibodies and the second library of nucleic acids encodes DARPins; or the first library of nucleic acids encodes monobodies and the second library of nucleic acids encodes scFv molecules. In this respect, a portion of the bivalent binding agent will be one type of binding agent molecule and the other portion of the bivalent binding agent will be another type of binding agent molecule.

Desirably, first and second library of nucleic acids encoding binding agents that bind to a target molecule are obtained from a primary selection or primary library screen for binding agents that bind to the target molecule of interest. For example, a library containing a diverse population of binding agents can be screened for binding to a target molecule of interest and binding agents that exhibit varying degrees of affinity for the target molecule can be pooled to create a population of binding agents of use in the method of the invention. Libraries can include, e.g., yeast, bacteria, bacteriophage or phagemid, virus, cell, ribosome, or a combination of such in vitro display systems. An exemplary cell-free display system is described in WO 01/05808. A ribosome display library is described by Groves, et al. ((2006) *J. Immunol. Meth.* 313:129-139). Phage display technology is well-known in the art (see, for example, WO 91/17271 or WO 92/001047). Phage used in such methods are typically filamentous phage including fd and M13 binding domains expressed from phage with the binding agent protein recombinantly fused to either the phage gene III or gene VIII protein.

Upon amplification of the first and second libraries of nucleic acids, a first pool and second pool of megaprimers are respectively generated. A megaprimer for the purposes of the present invention is intended to refer to an oligonucleotide that is in the range of, e.g., 100 to 1000 or more bases in length, and is capable of serving as a primer for enzymatic extension of nucleic acid molecules (e.g., the megaprimer is phosphorylated). Amplification of the nucleic acids encoding the binding agents can be carried out e.g., by conventional reverse-transcription (if the nucleic acids encoding the population of binding agents is RNA) and/or PCR amplification using primers, which flank the nucleic acids encoding the binding agent (e.g., vector sequences) or primers that hybridize to the 3' and 5' ends of the nucleic acids encoding the binding agent. Such primers can be readily designed by the skilled artisan based upon the known nucleic acid sequences encoding antibody fragments, single-domain antibodies, FHA domains, monobodies, minibodies, scFv, AFFIBODY molecules, affilins, anticalins, DARPins and nanofitins. For example, PCR amplification of the sequence encoding the $10^{th}$ subunit of human fibronectin type III repeat (FN3) has been described by Karatan, et al. ((2004) *Chem. Biol.* 11:835-44). Likewise, primer combinations for amplifying a majority of the known human antibody sequences is described by Yuan, et al. ((2013) *Neural Regen. Res.* 8:3107-3115).

Given that the present method is of use in generating a high affinity, bivalent binding agent with altered affinity and/or specificity for a target molecule, and/or altered solubility, protein folding, thermal stability etc., the step of amplifying the nucleic acids encoding the binding agents can be carried out via, e.g., error-prone PCR (Zaccolo, et al. (1996) *J. Mol. Biol.* 255:589-603) or mutagenic PCR (Cadwell & Joyce (1994) *PCR Methods Appl.* 3:S136-S140) to add more diversity through random mutation.

In the subsequent step of the method of the invention, the first and second pool of megaprimers are used in Kunkel mutagenesis (Kunkel, et al. (1991) *Methods Enzymol.* 204: 125-139; Huang, et al. (2012) *Methods* 58:10-17) to prime DNA synthesis with a phage-display vector as template (See FIG. 1, Step B). To facilitate subsequent screening, certain embodiments include removal of the template strand. This can be achieved by restriction enzymatic digestion and/or using an uracilated template strand, as exemplified herein. For example, the template phage-display vector can be replicated in the presence of uracil in an ung-/dut-*E. coli* strain, such as BW313 and CJ236, which are deficient in the enzyme dUTP pyrophosphatase (dut-) resulting in an increased incorporation of uracil in place of thymine in the DNA. Uracilated template DNA may also be prepared enzymatically using for example T7 DNA polymerase together with dNTP's and dUTP. Uracilated template DNA can then be removed by treatment with uracil-N-glycosylase (UDG), which hydrolyzes uracils in the heteroduplex.

Figure 2:
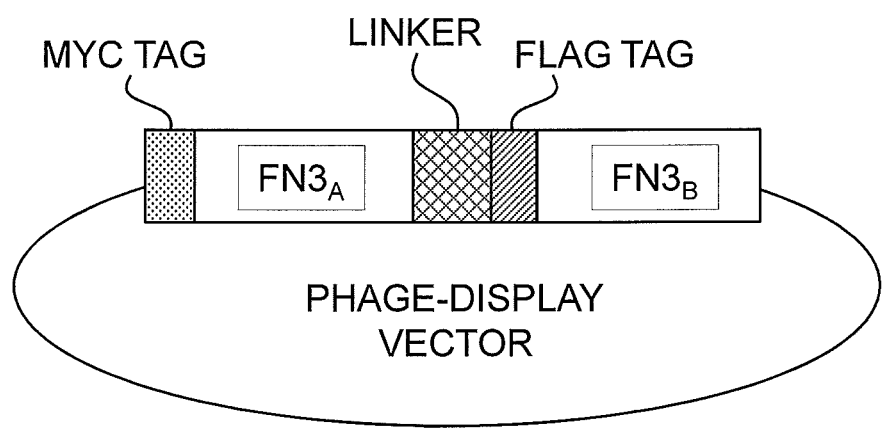
FIG. 2 depicts the general structure of a phage-display vector of a library for use in generating a FN3-based bivalent binding agent.
Figure 4:
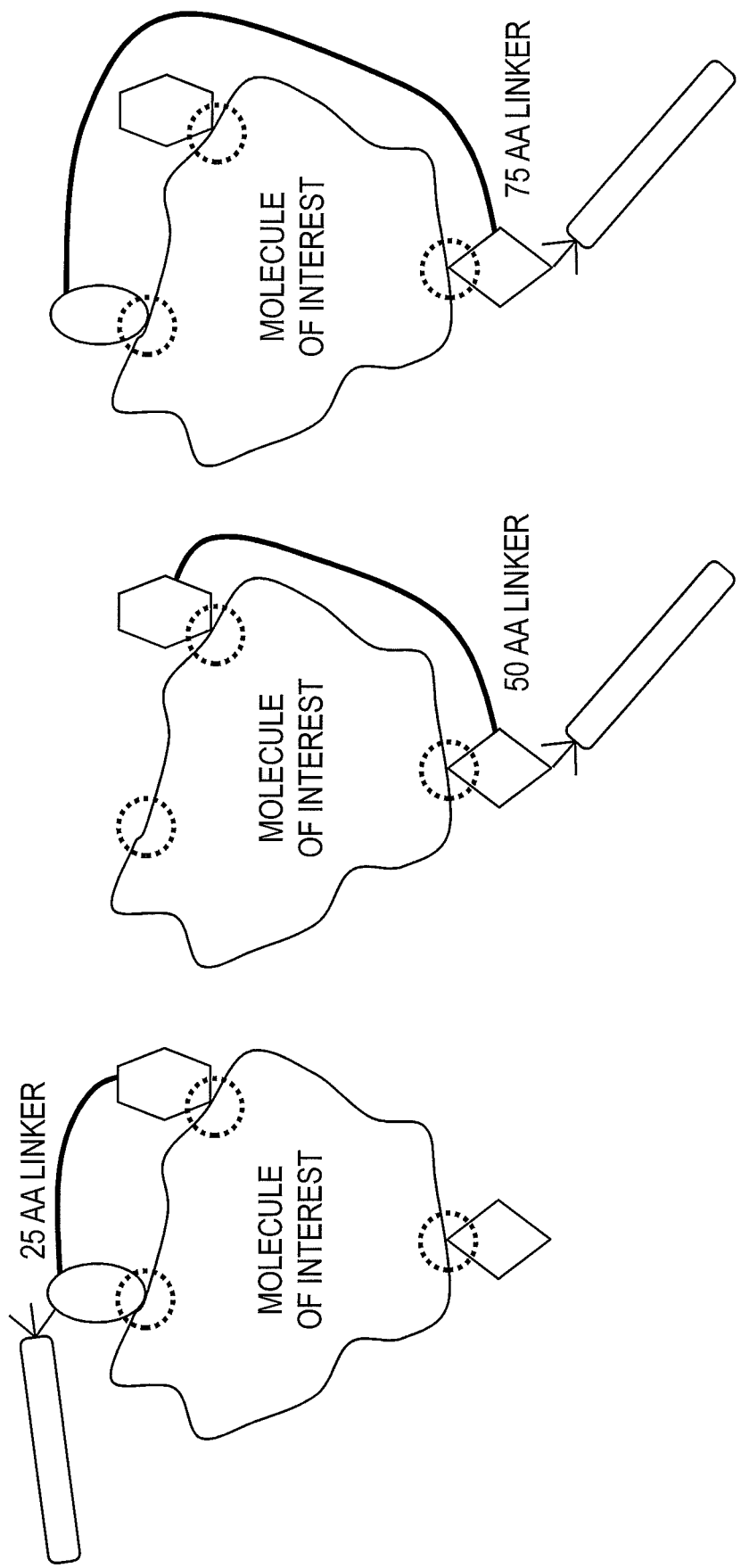
FIG. 4 illustrates the ability of using the instant method and library of phage display vectors to screen for bivalent reagents that bind to epitopes (dashed circle) located in near and distant locations on the same target molecule by simultaneously screening random binders (oval, hexagon and diamond) as well as random linkers of varying length (i.e., 25 amino acid (AA) residues, 50 AA residues and 75 AA residues).

To serve as a template for generating a bivalent binding agent, the nucleic acids of the phage-display vector harbors a first binding agent coding region and a second binding agent coding region, each of which is capable of hybridizing to a member of the first or second pool of megaprimers (see FIG. 2). In this respect, the first and second binding agent coding regions of the phage-display vector has one or more contiguous nucleic acid sequences that are complementary to sequences present in the megaprimers. Such complementary sequences can, e.g., be non-random sequences that are outside of the variable region sequences of the binding agents. Typically, there are about 15 to about 30 complementary nucleotides in the 5' end and about 15 to about 30 complementary nucleotides in the 3' end of the megaprimer relative to the first and second binding agent coding regions of the phage-display vector. However, shorter complementary segments may also be used. During this step, each of the megaprimers obtained in the previous step has an equal chance to anneal to the first and second binding agent coding regions within the phage-display vector, thus allowing many different combinations of binding agents from the populations of binding agents to now be linked together as bivalent molecules.

To ensure that the first and second binding agent coding regions do not interfere with subsequent screening for high affinity binding agents, the first and second binding agent coding regions further encode one or more stop codons (see FIG. 1, steps B and C). In certain embodiments, the stop codons are located within sequences encoding the variable region of the binding agent (see FIG. 3). In other embodiments, sequences encoding the variable region of the binding agent have restriction endonuclease recognition sites. As a result of annealing the megaprimers to the uracilated phage-display vector, the first binding agent coding region forms a heteroduplex with a first megaprimer and the second binding agent coding region forms a heteroduplex with a second megaprimer (See FIG. 1, Step B).

In some embodiments, the bivalent binding agent is composed of a single type of binding agent, e.g., antibody fragments, single-domain antibodies, FHA domains, monobodies, minibodies, scFv, AFFIBODY molecules, affilins, anticalins, DARPins or nanofitins, i.e., the first and second library of nucleic acids both encode a single type of binding agent. Therefore, in accordance with this embodiment, the first and second binding agent coding regions of the phage-display vector have substantially the same sequence. An exemplary phage display vector and nucleotide (SEQ ID NO:16) and deduced amino acid sequence (SEQ ID NOs: 17-20) of a phage-display vector encoding tandem FN3 proteins is respectively presented in FIG. 2 and FIG. 3.

In other embodiments, the bivalent binding agent is composed of a mixture of binding agents that bind to a target molecule of interest, i.e., the first and second library of nucleic acids both encode at least two different types of binding agents, e.g., the first library encodes monobodies and the second library encodes scFv. Therefore, the first and second binding agent coding regions of the phage-display vector are different. By way of illustration, the first binding agent coding region can encode a monobody, whereas the second binding agent coding region encodes for a scFv.

In further embodiments, the phage-display vectors encode a tag located upstream or downstream of one or both of the first and second binding agent coding regions. Such tags may be useful in purification, detection and/or screening and include, but not limited to, a FLAG®-tag (DYKDDDDK), polyhistidine-tag, a gD-tag, a c-myc tag, green fluorescence protein tag, a GST-tag or β-galactosidase tag. In certain embodiments, it is contemplated that a tag is located upstream of both the first and second binding agent coding regions, and said tags are different from one another.

To generate a bivalent binding agent, the first and second binding agent coding regions are tandemly arranged in the phage-display vectors and are linked via a nucleic acid molecule encoding a linker. A linker of the present invention serves the purpose of covalently attaching the first binding agent to the second binding agent at a distance appropriate for the first and second binding agents to simultaneously bind to their respective epitopes. Linkers of use in this invention can be as few as 5 amino acids in length, or 10 amino acids in length or 20 amino acids in length; or as many as 75 amino acids in length, 85 amino acids in length or 100 amino acids in length. The linker length may further be present within any range delimited by any pair of the foregoing values, such as between 20 and 75 amino acid residues, or between 10 and 85 amino acid residues, for example. Any one of the flexible, rigid, or cleavable linkers described herein can be used in the initial screen to identify a bivalent binding agent. Other examples of suitable linker are described by, e.g., LeGall, et al. (2004) *Prot. Eng. Design Select.* 17:357-366. In certain embodiments, the linker used in the initial screen for identifying bivalent binding agents is at least amino acids, or more preferably 50 amino acids in length.

A phage-display vector of the present invention is a vector containing phage-derived polynucleotide sequences capable of expressing, or conditionally expressing, a heterologous polypeptide, for example, as a fusion protein with a phage protein (e.g., a phage surface protein). In some embodiments, a phage-display vector of the present invention is a vector derived from a filamentous phage (e.g., phage f1, fd, and M13) or a bacteriophage (e.g., T7 bacteriophage or a lambdoid phage. Filamentous phage and bacteriophage are described by, e.g., Santini ((1998) *J. Mol. Biol.* 282:125-135), Rosenberg, et al. ((1996) *Innovations* 6:1-6), and Houshmand, et al. ((1999) *Anal. Biochem.* 268:363-370).

In general, a phage-display vector of the invention can include the following elements: a promoter suited for constitutive or inducible expression (e.g., lac promoter); a ribosome binding site and signal sequence preceding the sequence encoding a displayed peptide; and one or more restriction sites; optionally, a tag sequence such as a stretch of 5-6 histidines or an epitope recognized by an antibody; a second tag sequence; a suppressible codon (e.g., a termination codon); and a sequence encoding a phage surface protein positioned in-frame to form a fusion with the bivalent binding agent to be displayed. In general, a phage-display vector of the invention contains a promoter and/or regulatory region operably linked to a polynucleotide sequence encoding the bivalent binding agent and a sequence encoding a phage surface protein.

The term "operably linked" refers to a functional linkage between nucleic acid sequences such that the linked promoter and/or regulatory region functionally controls expression of the coding sequence. It also refers to the linkage between coding sequences such that they may be controlled by the same promoter and/or regulatory region. Such linkage between coding sequences may also be referred to as being linked in-frame or in the same coding frame such that a fusion protein comprising the amino acids encoded by the coding sequences may be expressed.

In other embodiments of the invention, the ability of the phage-display vector to express a fusion protein is regulated in part by use of a regulated promoter or other regulatory region (e.g., an inducible promoter such that in the absence of induction, expression is low or undetectable). Non-limiting examples of inducible promoters include the lac promoter, the lac UV5 promoter, the arabinose promoter, and the tet promoter. In some embodiments, an inducible promoter can be further restricted by incorporating repressors (e.g., lacI) or terminators (e.g., a tHP terminator). For example, repressor lacI can be used together with the Lac promoter.

As used herein, the term "phage surface protein" refers to any protein normally found at the surface of a filamentous phage (e.g., phage f1, fd, and M13) or a bacteriophage (e.g., λ, T4 and T7) that can be adapted to be expressed as a fusion protein with a heterologous polypeptide and still be assembled into a phage particle such that the polypeptide is displayed on the surface of the phage. Suitable surface proteins derived from filamentous phages include, but are not limited to, minor coat proteins from filamentous phages, such as gene III proteins and gene VIII proteins; major coat proteins from filamentous phages such as, gene VI proteins, gene VII proteins, gene IX proteins; gene 10 proteins from T7; and capsid D protein (gpD) of bacteriophage λ. In some embodiments, a suitable phage surface protein is a domain, a truncated version, a fragment, or a functional variant of a naturally occurring surface protein. For example, a suitable phage surface protein can be a domain of the gene III protein, e.g., the anchor domain or "stump." Additional exemplary phage surface proteins are described in WO 00/71694. As appreciated by the skilled artisan, the choice of a phage surface protein is to be made in combination with a consideration of the phage-display vector and the cell to be used for propagation thereof.

Any peptide sequences capable of driving or directing secretion of expressed protein or polypeptide can be used as signal sequence for the phage-display vector of the invention. Exemplary leader sequences include, but not limited to, a PelB leader sequence and an OmpA leader sequence.

General methods for constructing phage-display vectors, phage-display libraries and the method of use are described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard, et al. (1999) *J. Biol. Chem.* 274:18218-30; Hoogenboom, et al. (1998) *Immunotechnoloqy* 4:1-20; Hoogenboom, et al. (2000) *Immunol. Today* 2:371-8; Fuchs, et al. (1991) *Bio/Technology* 9:1370-1372; Huse, et al. (1989) *Science* 246:1275-1281; Griffiths, et al. (1993) *EMBO J.* 12:725-734; Hawkins, et al. (1992) *J. Mol. Biol.* 226:889-896; Clackson, et al. (1991) *Nature* 352:624-628; Gram, et al. (1992) *PNAS* 89:3576-3580; Garrard, et al. (1991) *Bio/Technology* 9:1373-1377; Rebar, et al. (1996) *Methods Enzymol.* 267: 129-49; Hoogenboom, et al. (1991) *Nucl. Acid Res.* 19:4133-4137; and Barbas, et al. (1991) *PNAS* 88:7978-7982.

Once the reverse-transcribed/PCR-amplified megaprimers are annealed to the uracilated phage-display vector, the first and second pool of megaprimers are extended in the presence of a DNA polymerase (e.g., T7 or T4 polymerase) and ligated with a DNA ligase (e.g., T4 ligase) to generate a heteroduplex phage-display library, i.e., covalently closed circular DNA (cccDNA), in which one stand is the template strand and the other, in vitro synthesized strand, encodes a bivalent binding agent of interest (see FIG. 1, Step C). Upon transformation into an appropriate host cell (e.g., *E. coli*), the uracilated parent strand (containing stop codons and restriction sites within the coding region) is degraded by the host cell leaving the recombinant strand coding for a pair of binding agents that are now linked.

Once prepared, the phage-display library is subsequently screened to identify bivalent phage clones of the library that simultaneously bind to different epitopes of the target molecule of interest (see FIG. 1, Step D). The phage-display library screening step is carried out by inducing the phage to display the bivalent binding agents on the surface of the phage clones and identifying bivalent binding agents that bind to the target molecule. Any suitable method that detects interactions between molecules can be used to identify bivalent binding agents of interest including, e.g., ELISA, co-immunoprecipitation, bimolecular fluorescence complementation, affinity electrophoresis, pull-down assays, label transfer, and the like. However, in certain embodiments, the screen is carried out using a tagged target molecule. For example, a biotin-tagged target molecule can be contacted with the library of phage-displayed bivalent binding agents, and bivalent binding agent-target molecule complexes are captured using streptavidin-coated magnetic beads. Advantageously, any unbound phage-displayed bivalent binding agents can be removed by washing the magnetic beads. Alternatively, or in addition to, the inclusion of a calmodulin binding peptide in a flexible linker allows for the removal of binding agents that fail to bind to two different locations on the target molecule based upon binding to calmodulin-coated beads in the presence of calcium.

Target molecules that can be used in accordance with this invention include proteins, glycoproteins, phosphoproteins, other post-translationally modified proteins, protein complexes, nucleic acids, protein:nucleic acid complexes, carbohydrates, lipid complexes, organic and inorganic molecules, including natural and synthetic versions of any such molecules. The target or target molecules may include a single protein or other biomolecule or multiple molecules (e.g., in a multi-molecular complex). As described herein, target molecules can be tagged to facilitate detection and immobilization of bivalent binding agents of interest. Such tags include, e.g., a His-tag, FLAG®-tag (DYKDDDDK), V5-tag, HA-tag, or c-myc-tag. In particular embodiments, the target molecule is biotinylated.

The bivalent binding agent identified by the method of this invention can be used as is or one or both binding agents of the bivalent molecule can be further modified and screened for improved binding, e.g., by directed evolution. Whether used directly or after further modification, the high affinity, bivalent binding agents of this invention are of particular use in sandwich assays. Accordingly, once a suitable bivalent binding agent is identified, the first binding agent and/or second binding agent is conjugated or attached to a member of a sandwich assay. In some embodiments, the sandwich assay is a heterogeneous sandwich assay. In other embodiments, the sandwich assay is a homogenous sandwich assay.

A heterogeneous sandwich assay is an immunoassay in which a first binding agent (i.e., capture reagent) is bound to a solid support member such as microplate or immunosensor surface, allowing the retention of a target molecule while unbound molecules are removed by washing. The presence of the target molecule bound to the solid support member via the first binding agent is then determined by applying a second binding agent, which is directly or indirectly labeled or tagged with a reporter member. Generally, the reporter member provides a detectable signal (e.g., an optical or radioactive signal), which is measured with an appropriate reader, e.g., an electronic plate reader such as an ELISA-plate reader.

Any suitable materials can serve as a solid support for reversible immobilization of the first binding agent used for the capture of a target molecule of interest. The immobilizing support can be any surface composed of, e.g., polystyrene, polyethylene, polycarbonate, perfluorocarbon polymer, glass, or latex and can be in the form of a plate (e.g. a microtiter plate), coated magnetic particle, polymeric bead or latex particle. Conjugation or linkage of proteins to such solid supports is routine in the art and any suitable cross-linking agent may be used.

A reporter member is any compound, which is capable of directly or indirectly generating a measurable signal detectable by external means. Reporter members include enzymes (e.g., horseradish peroxidase or alkaline phosphatase, which are detectable via chromogenic substrates), radioisotopes (e.g., $^{125}$I), luminescent materials, biotin/streptavidin, chromogens, fluorophores, metal (e.g., lanthanide), coenzymes, and enzyme inhibitors. In most cases, the choice of reporter is not central to the method. Reporters that are conventionally conjugated to antibodies such as FITC or rhodamine for a fluorescent signal can usually be replaced with enzymes such as alkaline phosphatase or horse radish peroxidase if a calorimetric assay is desired, or with enzymes such as carbonic anhydrase or urease for conductivity assays. The reporter can be conjugated or attached to the second binding agent by any appropriate means. For example, wherein the reporter is a protein (e.g., an enzyme), the protein can be conjugated to the second binding agent by coexpressing the reporter protein and second binding agent as a fusion protein. By way of further illustration, a fluorophore can be conjugated to the second binding agent using an amine-reactive fluorophore.

Alternatively, a commonly used alternative to conjugating the reporter directly to the second binding agent, is to employ a secondary antibody conjugated to the reporter. In accordance with the present invention, a secondary antibody is an antibody developed to bind to the second binding agent. If the secondary antibody is conjugated to a reporter, then the binding of the secondary antibody to the second binding agent provides attachment of the reporter indirectly to the second binding agent without chemical conjugation.

In contrast to a heterogenous sandwich assay where unbound molecules are removed, a homogeneous sandwich assay does not require this separation because the signal is generated when the binding occurs. More specifically, homogenous sandwich assays generally rely on protein-protein interactions which bring a donor-acceptor pair into close proximity (e.g., 10 to 100 Å) in order to generate the desired signal. Well-known examples of donor-acceptor pairs include those based on based on fluorescence resonance energy transfer (FRET), bioluminescence resonance energy transfer (BRET), and crab-claw sandwich enzymatic complementation immunoassay (CS-ECIA).

As is known in the art, FRET is a physical phenomenon in which a donor fluorophore in its excited state non-radiatively transfers its excitation energy to a neighboring acceptor fluorophore, thereby causing the acceptor to emit its characteristic fluorescence. Numerous dye fluorophores and fluorescent protein donors and acceptors FRET pairs have been described in the art and can be used in accordance with this invention. By way of illustration, members of FRET assays can include green fluorescent protein (GFP) and its blue-fluorescent mutant, BFP; GFP paired with a cyan fluorescent protein (CFP), GFP paired with a yellow-green fluorescent protein (YFP), and the like. For selection of appropriate FRET pairs, see, e.g., Bajar, et al. (2016) *Sensors (Basel)* 16(9):1488. BRET relies upon non-radiative energy transfer between the *Renilla* luciferase (Rluc) as energy donor and a fluorescent protein as energy acceptor. A typical energy acceptor member used in BRET experiments, which fulfills these criteria, is YFP (BRET1 version). In BRET2 assays, YFP has been replaced by GPF2, a GFP mutant that can be excited at 400 nm. Additional BRET assays include eBRET2, BRET3 and QD-BRET, each of which are known in the art and described, e.g., by Borroto-Escuela, et al. ((2013) *Methods Cell Biol.* 117:141-64).

CS-ECIA is based upon the use of an N-terminal deletion mutant (Δα, i.e., donor member) and C-terminal deletion mutant (Δω, i.e., acceptor member) of β-galactosidase (β-gal), each fused to a binding agent, wherein upon binding to a common target molecule, the binding agents bring the two mutants of β-gal into proximity thereby allowing reassociation of the β-gal enzyme. The resulting enzymatic complementation is measured as an increase in β-gal activity using a suitable fluorescent or luminescent substrate. See, e.g., Komiya, et al. (2004) *Anal. Biochem.* 327:241-6. In a similar approach, inactive N- and C-terminal fragments of *Gaussia* luciferase have been used in an enzymatic complementation immunoassay. See Luker & Luker (2014) *Meth. Mol. Biol.* 1098:59-69.

Conjugation of homogenous sandwich assay dyes to the first and/or second binding agent can be carried out using conventional reactive groups and methods. See, e.g., Sapsford, et al. (2006) *Angew Chem. Int. Ed.* 45:4562-88. Similarly, conjugation of protein-based donor-acceptor pairs to the first and/or second binding agent can be carried out by conventional recombinant protein methods to generate fusion proteins.

The high affinity, bivalent binding agents conjugated to (i) a substrate and optionally a reporter member; or (ii) to a donor-acceptor find particular use in a variety of sandwich assays including, but not limited to, diagnostic assays, in vivo imaging, cell killing, cell sorting, and cell or tissue staining. Depending on the particular application of the bivalent binding agent, the first and second binding agents may remain linked or the first and second binding agents may be separated (e.g., by cleaving the linker or by expression of each binding agent separately).

In some embodiments, the linker used in the generation of the bivalent binding agent may likewise be used in generating the conjugates disclosed herein so that appropriate spacing is retained.

In other embodiments, the linker is modified to provide optimal spacing between the first and second binding agents when bound to their cognate epitopes. Accordingly, in certain embodiments, the bivalent binding agent generated in the method of the invention is further screened in conjunction with a library of linkers. More specifically, a suitable linker for linking the first and second binding agents may be identified by (i) amplifying nucleic acid encoding the first and second binding agents to generate megaprimers; (ii) annealing the megaprimers of (i) to a library of single-stranded phage-display vectors harboring a randomized library of linkers so that the first and second binding agent coding regions are in tandem and linked via a member of the randomized library of linkers; (iii) primer extending the megaprimers of (ii) to generate a phage-display library of bivalent phage clones; and (iv) screening the phage-display library to identify a bivalent binding agent that binds to different epitopes on the target molecule and contains a suitable linker length and sequence for maximum binding affinity and specificity.

The linker library used in this aspect of the invention is composed of a suite of vectors that include random linker lengths and sequences. The linkers of the randomized library of linkers may be based upon conventional flexible, rigid or cleavable linker sequences or variants or combinations thereof. See, e.g., LeGall, et al. (2004) *Prot. Eng. Design Select.* 17:357-366. In addition, the linker may be designed to incorporate an amino acid or short sequence that serves as a cleavable site for a protease that can be used to separate the first and second binding agents from one another at an appropriate time. The complexity of the linker sequences obtained in the population or "library" can be pre-determined or random. In certain embodiments, the library of linkers is composed of less than 10 different linkers, more preferably less than 5 different linkers, most preferably less three different linkers. In particular embodiments, the library of linkers is composed of linkers having a length of 25, 50 and 75 amino acid residues.

A flexible linker refers to an amino acid sequence that allows the adjacent first and second binding agents to move freely relative to one another. Flexible linkers have conventionally included glycine and optionally serine residues. By way of illustration, a library of flexible linkers can be based upon a $(GGGGS)_n$ motif (Chen, et al. (2013) *Adv. Drug Deliv. Rev.* 65:1357-69), wherein said library includes vectors with as few as one repeat of the GGGGS motif to vectors that include as many as 5, 10, 15, or 20 of the GGGGS motifs in tandem resulting in linkers of 5, 50, 75 and 100 amino acids in length, respectively. FIG. illustrates the effect of including linkers of varying lengths to identify bivalent binding agents which bind to close and distant epitopes on a target molecule of interest. Other flexible linkers include, but are not to, homoglycine, SAKTTPKLGG (SEQ ID NO:3) or variants thereof, RADAAPTVS and variants thereof such as RADAAAAGGPGS (SEQ ID NO:4) and RADAAAA ($G_4S$)$_4$ (SEQ ID NO:5).

In certain embodiments, the flexible linker includes at least one calmodulin binding peptide (e.g., a M13 helix peptide). As described herein, when both binding agents of the tandem dimer are bound to the target molecule, the calmodulin binding peptide does not to bind to calmodulin due to torsion on the helix. Therefore, any binding agents that fail to bind to two different locations on the target molecule can be readily removed via calmodulin-coated beads in the presence of calcium. In some embodiments, the flexible linker includes at least one calmodulin binding peptide. In other embodiments, the flexible linker includes at least two calmodulin binding peptides in tandem. The flexible linker may be composed solely of the calmodulin binding peptide(s) or be inserted within the sequence of another flexible linker. In certain embodiments, the calmodulin binding peptide has the amino acid sequence KRRWKKNFIAVSAANRFKKISSSGAL (SEQ ID NO:6) or a variant thereof that binds to calmodulin.

A rigid linker refers to an amino acid sequence that restricts movement of the adjacent first and second binding agents. Rigid linkers including proline or lysine residues are well-known in the art. By way of illustration, a library of rigid linkers can be based upon a (EAAAK)$_n$ motif, wherein said library includes vectors with as few as one repeat of the EAAAK motif to vectors that include as many as 5, 10, 15, or 20 of the EAAAK motifs in tandem, or disrupted by the sequence ALEA, resulting in linkers of varying lengths. Another rigid linker may be based upon repeating units of the sequence Ala-Pro.

Combinations of flexible and rigid linkers are also included in this invention. For example, combinations of different Gly-Ser segments may be combined with proline-rich rigid segments. See, e.g., U.S. Pat. No. 9,458,244, which discloses linkers composed of combinations of flexible GGGSG and GGSGG linkers and repeating units of Thr-Pro, Ala-Pro, and Leu-Pro as rigid segments.

Cleavable linkers refer to amino acid sequences that include protease recognition sequence, which allow for separation of the first and second binding agents. Exemplary cleavable linkers include, e.g., the sequences VSQTSKL-TR↓AETVFPDV (SEQ ID NO:7), PLG↓LWA, GGIEGR↓GS, AGNRVRR↓SVG (SEQ ID NO:8), and TRHRQPR↓GWE (SEQ ID NO:9), wherein arrow indicate the location of cleavage.

To facilitate the use of the bivalent binding agent and/or first and second binding agents of this invention, a kit is also provided. The kit includes a first binding agent and second binding agent that bind to different epitopes on a target molecule, wherein said first binding agent and second binding agent are separate or linked in tandem by a linker, e.g., a rigid linker, flexible linker, cleavable linker, or a combination thereof. In some embodiments, the first binding agent is conjugated to a solid support member and the second binding agent is optionally conjugated to a reporter member of a heterogenous sandwich assay. In other embodiments, the first and second binding agents are conjugated to a donor member and acceptor member of a homogeneous sandwich assay.

In addition to the binding agents, the kit can include substrates (e.g., for heterogenous sandwich assays), a protease for cleaving the first and second binding agents, wash buffers (e.g. for heterogenous sandwich assays), strepavidin-coated magnetic beads (e.g., where the second binding agent is conjugated to biotin), reaction/storage buffers, elution solutions, and the like.

The following non-limiting examples are provided to further illustrate the present invention.

Example 1: Identification of Bivalent Binding Agent to Pak1

A phage-display vector was designed, which included tandem FN3 sequences containing FLAG® (DYKDDDDK) and Myc tags for detection/capture (FIG. 2), as well as a flexible linker between the monobody sequences. In addition, to two stop codons (TAA and TGA) and StuI restriction sites were introduced into each BC and FG loop regions of the FN3 coding sequences to facilitate removal of the parent template and prevent display of the wild-type FN3 domain. More specifically, FN3 sequences were amplified with forward (5'-atg gcc gtt tct gat gtt ccg cgt a-3'; SEQ ID NO:10) and reverse (5'-gcc gct ggt acg gta gtt aat cga g-3'; SEQ ID NO:11) FN3 primers and cloned in tandem into the pAP-III$_A$ phagemid vector (Pershad, et al. (2011) *Anal. Biochem.* 412:210-16; Haidaris, et al. (2001) *J. Immunol. Methods* 257:185-202) using SLiCE (Seamless Ligation Cloning Extract) methodology (Zhang, et al. (2014) *Methods Mol. Biol.* 1116:235-44). The recombinant vector was transformed into the *E. coli* strain TG1 (Lucigen, Madison, Wis.), which encodes wild-type versions of dUTPase and uracil-N glyosylase, to propagate the newly synthesized vector. Eight clones were selected for sequence analysis and six of the eight were identified as containing the tandem FN3 sequences (FIG. 3). Recombinant clones were introduced into *E. coli* strain CJ236 (New England BioLabs, Ipswich, Mass.), which lacks functional dUTPase and uracil-N glycosylase, to generate an uracilated, single-stranded phage-display template vector.

To demonstrate the generation of a bivalent binding agent using the method of the invention, nucleic acid sequences encoding C12 and A9 monobodies (Huang, et al. (2012) *Methods* 58:10-17), which bind different epitopes of Pak1 kinase, were amplified with forward and reverse FN3 primers to generate a pool of megaprimers. The megaprimers were annealed to the uracilated, single-stranded phage-display template vector and primer extended. The primer extension was performed in accordance with known methods (Huang, et al. (2012) *Methods* 58:10-17). Briefly, 15 pmol of megaprimer was phosphorylated for 1 hour at 37° C. The phosphorylated megaprimer was annealed to 5 pmol of uracilated ssDNA phagemid by denaturing at 95° C. for 2 minutes and slowly reducing the temperature by 1° C. per minute until 24° C. was reached. To fill in the remaining portions of the plasmid, the heteroduplexes were extended by the action of T7 DNA Polymerase (New England Biolabs) and T4 DNA Ligase (New England Biolabs). The resulting double-stranded DNA was purified on a QIA-QUICK column and transformed by electroporation into 2×100 μL of the TG-1 strain of *E. coli* cells. Cells were allowed to recover at 150 rpm in 2 mL of warmed Recovery Media (Lucigen) for 30 minutes at 37° C. Cells were plated on two large 2×YT/Cb agar plates and incubated overnight at 30° C.

For phage display and screening, each plate was scraped into 5 mL of 2×YT media and the cells were combined and vortexed. Fifty microliters were used to inoculate 50 mL of 2×YT/Cb and grown to mid-log phase ($OD_{600}$=~0.4). Cells were infected with M13K07 helper phage at an MOI of 10 for 30 minutes at 37° C. Cells were spun down at 4,000 rpm for 7 minutes and resuspended in 2×YT/CB/Kan media. The culture was shaken at room temperature for 18 hours. The overnight culture was spun down twice at 12,000 rpm for 10 minutes and the 50 mL supernatant was precipitated with 10 mL of 24% PEG, 3 M NaCl, and 4% PEG (final), for 20 minutes at room temperature. The precipitate was spun down at 12,000 rpm for 10 minutes to pellet the phage. The tubes were rinsed with 1 mL of PBS each, and the pellet was resuspended in 1 mL of PBS.

The phage particles were subsequently screened for expression of bivalent binding agents. MAXISORP 96-well microtiter plates were coated overnight with 1 µg/mL NEUTRAVIDIN (Thermo Scientific) at 4° C. The plates were blocked the next day with 200 µL of 1% casein blocking buffer in PBS (Thermo Scientific) for 1 hour. All washings were carried out in 300 µL of PBST, three times each, using a BIOTEK ELx405 plate washer. Plates were washed before addition of 50 µL of 1-10 nM biotinylated Pak1 in PBST for 1 hour with 500 rpm shaking. Plates were washed and the phage culture spun down for 5 minutes at 4,000 rpm and the supernatant diluted 1:1 with PBST before adding a total of 50 µL/well. This was incubated for 1 hour shaking. Plates were washed and 50 µL/well of 1:5000 anti-M13-HRP bacteriophage monoclonal antibody (GE HealthCare) in PBST was added to all wells for 1 hour with shaking. The final wash was performed 5 times and to each well was added 50 µL of the ABTS with 0.03% $H_2O_2$. Plates were read at absorbance 405 nm after 5, 15, and 30 minutes using a POLARSTAR OPTIMA microplate reader (BMG Labtech). The results of this analysis indicated that multiple clones in the tandem phage library displayed the c-myc tag and recognized Pak1. In particular, a 78% (37/47) recombination rate was achieved. Five of the recombinant clones were subjected to sequence analysis, which revealed that all four possible combinations of bivalent molecules were present in the phage-display library (Table 1).

TABLE 1

| Clone Designation | Conformation (N-terminus FN3-FN3-C-terminus) |
|---|---|
| 1 | C12-A9 |
| 2 | C12-A9 |

TABLE 1-continued

| Clone Designation | Conformation (N-terminus FN3-FN3-C-terminus) |
|---|---|
| 3 | A9-C12 |
| 4 | A9-A9 |
| 5 | C12-C12 |

In a different experiment, a pool of monobodies enriched from the affinity selection against Pak1 kinase domain was amplified by PCR to generate megaprimers. Using the method described herein, the megaprimers were used to generate a bivalent tandem display library of $2 \times 10^7$ in size. The library was affinity-selected for two rounds and multiple clones were screened by phage ELISA to identify clones of higher affinities. Four clones with high ELISA values were sequenced and the sequences of their variable loops were listed in Table 2. Their sequences reveal that these clones share some conserved sequences, such as XKKTR and XXHVY in BC loop and ASWPW in FG loop. Their sequences also suggest that sequences in FN3-1 and FN3-2 are interchangeable (FN3-1 of B3 and D3 share similar sequences as FN3-2 of E5 and F10; the FN3-2 of B3 and D3 are similar to the FN3-1 of E5 and F10).

TABLE 2

|  | FN3-1 | | FN3-2 | |
|---|---|---|---|---|
| Clone | BC loop 1 | FG loop 1 | BC loop 2 | FG loop 2 |
| B3 | CKKTR | ASWPW | ECHMH | DTRHY |
| D3 | WKKTR | ASWPW | SRHIY | DLYSN |
| E5 | WVHVY | WCSHL | LRKTS | ASWPW |
| F10 | RQHVY | HFTHP | WKKTR | ASWPW |

A competitive phage ELISA was used to estimate the half maximal inhibitory concentration ($IC_H$) of Clone D3. In this assay, the target (biotinylated Pak1) was immobilized on an ELISA plate. Varying concentrations of competitor (non-biotinylated Pak1) were mixed with phage particles displaying the bivalent binding agent and subsequently applied to the immobilized target. This analysis indicated that the $IC_H$ of Clone D3 was ~1.5 nM, which is a 1000-fold improvement over the binding of the monobodies from the primary screen, which had a $K_D$ (~$IC_{50}$) in the single digit µM range. Therefore, each domain can bind simultaneously to the Pak1 target protein.

Example 2: Kit for MegaSTAR

Kit primers for amplifying nucleic acids encoding a population of binding agents that bind to a target molecule (Table 3).

TABLE 3

| Scaffold | Primer | Sequence (5'→3') | SEQ ID NO: |
|---|---|---|---|
| Monobody (FN3) | Forward | atggccgtttctgatgttccgcgta | 10 |
| | Reverse | gccgctggtacggtagttaatcgag | 11 |
| Affilin (gamma-B crystallin) | Forward | atggggaagatcacttttttacgaggac | 12 |
| | Reverse | tcaataaaaatccatcaccccgtcttaaagaacc | 13 |
| DARPin | Forward | atgagaggatcgcatcaccatcaccatcac* | 14 |

TABLE 3-continued

| Scaffold | Primer | Sequence (5'→3') | SEQ ID NO: |
|---|---|---|---|
| | Reverse | ttaattaagcttttgcaggatttcagc cagg | 15 |

*Includes sequences encoding His₆tag.

The kit also includes a single-stranded, phage-display vector containing first and second binding agent coding regions each encoding for a binding agent linked in tandem via a nucleic acid molecule encoding a flexible linker. Exemplary phage-display vector inserts (defined by the resulting fusion protein) and corresponding primers included in the kit include, but are not limited to, the combinations listed in Table 4. As the skilled artisan would appreciate, the N- and C-terminal orientations of the binding agents listed in Table 3 can be readily reversed.

TABLE 4

| Phage Display Vector Insert (N-terminus–>C-terminus) | Primers |
|---|---|
| Monobody-linker-Monobody | Monobody |
| Monobody-linker-DARPin | Monobody, DARPin |
| DARPin-Linker-DARPin | DARPin |
| Monobody-Linker-Affilin | Monobody, Affilin |
| Affilin-Linker-Affilin | Affilin |
| DARPin-Linker Affilin | DARPin, Affilin |

Example 3: Selection of Tandem Dimers

To facilitate the isolation of tandem dimers (i.e., bivalent binding agents that bind to different locations on the target molecule), a helix peptide can be inserted into the flexible linker located between the first and second binding agent coding regions. By way of illustration, an M13 calmodulin binding peptide (residues 577-602 of skeletal muscle myosin light chain kinase; Blumenthal, et al. (1985) *Proc. Natl. Acad. Sci. USA* 82:3187-91) could be used. In this respect, when both domains of the tandem dimer are bound to the target molecule, the M13 helix peptide would not be able to bind to calmodulin due to torsion on the helix. Therefore, any binding agents that fail to bind to two different locations on the target molecule can be readily removed via calmodulin-coated beads in the presence of calcium.

What is claimed is:

1. A method for generating a high affinity, bivalent binding agent for a sandwich assay comprising:
  (a) amplifying a first and second library of nucleic acids, each library encoding a population of binding agents that bind to different epitopes on a target molecule, to generate a first and second pool of megaprimers;
  (b) annealing the first and second pool of megaprimers of (a) to a single-stranded, uracilated phage-display vector comprising a first binding agent coding region and second binding agent coding region each capable of hybridizing to the first or second pool of megaprimers, wherein the first and second binding agent coding regions are in tandem and linked via a linker;
  (c) primer extending the first and second pool of megaprimers of (b) to generate a phage-display library of bivalent phage clones;
  (d) screening the phage-display library to identify a bivalent binding agent comprising a first binding agent and second binding agent, each of which binds to a different epitope on the target molecule; and
  (e) conjugating the first or second binding agent to a member of a sandwich assay.

2. The method of claim 1, wherein the population of binding agents comprises a library of antibody fragments, single-domain antibodies, Forkhead-Associated domains, monobodies, minibodies, single-chain variable fragments, AFFIBODY molecules, affilins, anticalins, designed ankyrin repeat proteins, nanofitins, linear peptides or a combination thereof.

3. The method of claim 1, wherein step (d) further comprises:
  (i) amplifying nucleic acid encoding the first and second binding agents to generate megaprimers;
  (ii) annealing the megaprimers of (i) to a library of single-stranded phage-display vectors comprising a randomized library of linkers so that the first and second binding agent coding regions are in tandem and linked via a member of the randomized library of linkers;
  (iii) primer extending the megaprimers of (ii) to generate a phage-display library of bivalent phage clones; and
  (iv) screening the phage-display library to identify a bivalent binding agent that binds to different epitopes on the target molecule.

4. The method of claim 3, wherein the randomized library of linkers comprises rigid linkers, flexible linkers, cleavable linkers, or a combination thereof.

5. The method of claim 4, wherein the flexible linkers further comprise a calmodulin binding peptide.

6. The method of claim 1, wherein the first binding agent is conjugated to a solid support member and the second binding agent is optionally conjugated to a reporter member of a heterogenous sandwich assay.

7. The method of claim 1, wherein the first and second binding agents are conjugated to a donor member and acceptor member of a homogeneous sandwich assay.

8. The method of claim 1, wherein the first and second binding agents are separated prior to the step of conjugating the first or second binding agent to a member of a sandwich assay.

9. A kit comprising the first and second binding agents generated by the method of claim 1 or 8, wherein the first and second binding agents are different types of binding agents selected from the group consisting of antibody fragments, single-domain antibodies, Forkhead-Associated domains, monobodies, minibodies, single-chain variable fragments, AFFIBODY molecules, affilins, anticalins, designed ankyrin repeat proteins, nanofitins, and linear peptides, wherein the first and second binding agents are conjugated to a donor member and acceptor member of a homogeneous sandwich assay.

10. A kit comprising the first and second binding agents generated by the method of claim 1, wherein the first and second binding agents are in tandem and linked via a flexible linker comprising at least one calmodulin binding peptide.

11. A method for generating a high affinity, bivalent binding agent for a sandwich assay comprising:
  (a) amplifying a first and second library of nucleic acids, each library encoding a population of binding agents that bind to different epitopes on a target molecule, to generate a first and second pool of megaprimers;
  (b) annealing the first and second pool of megaprimers of (a) to a single-stranded, uracilated phage-display vector comprising a first binding agent coding region and second binding agent coding region each capable of hybridizing to the first or second pool of megaprimers, wherein the first and second binding agent coding regions are in tandem and linked via a linker;
  (c) primer extending the first and second pool of megaprimers of (b) to generate a phage-display library of bivalent phage clones; and
  (d) screening the phage-display library to identify a bivalent binding agent comprising a first binding agent and second binding agent, each of which binds to a different epitope on the target molecule.

12. The method of claim 11, wherein the population of binding agents comprises a library of antibody fragments, single-domain antibodies, Forkhead-Associated domains, monobodies, minibodies, single-chain variable fragments, AFFIBODY molecules, affilins, anticalins, designed ankyrin repeat proteins, nanofitins, linear peptides or a combination thereof.

13. The method of claim 11, wherein step (d) further comprises:
  (i) amplifying nucleic acid encoding the first and second binding agents to generate megaprimers;
  (ii) annealing the megaprimers of (i) to a library of single-stranded phage-display vectors comprising a randomized library of linkers so that the first and second binding agent coding regions are in tandem and linked via a member of the randomized library of linkers;
  (iii) primer extending the megaprimers of (ii) to generate a phage-display library of bivalent phage clones; and
  (iv) screening the phage-display library to identify a bivalent binding agent that binds to different epitopes on the target molecule.

14. The method of claim 13, wherein the randomized library of linkers comprises rigid linkers, flexible linkers, cleavable linkers, or a combination thereof.

15. The method of claim 14, wherein the flexible linkers further comprise a calmodulin binding peptide.

* * * * *

SEQUENCE LISTING

```
<160> NUMBER OF SEQ ID NOS: 20

<210> SEQ ID NO 1
<211> LENGTH: 94
<212> TYPE: PRT
<213> ORGANISM: Artificial Sequence
<220> FEATURE:
<223> OTHER INFORMATION: Synthetic polypeptide

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 94
<212> TYPE: PRT
<213> ORGANISM: Artificial Sequence
<220> FEATURE:
<223> OTHER INFORMATION: Synthetic polypeptide

<400> SEQUENCE: 2
```

```
Met Ala Val Ser Asp Val Pro Arg Lys Leu Glu Val Val Ala Ala Thr
1               5                   10                  15

Pro Thr Ser Leu Leu Ile Ser Trp Asp Ala Pro Cys Arg Lys Cys Leu
            20                  25                  30

Tyr Tyr Arg Ile Thr Tyr Gly Glu Thr Gly Gly Asn Ser Pro Val Gln
                35                  40                  45

Glu Phe Thr Val Pro Gly Ser Lys Ser Thr Ala Thr Ile Ser Gly Leu
    50                  55                  60

Lys Pro Gly Val Asp Tyr Thr Ile Thr Val Tyr Ala Val Thr Arg Leu
65                  70                  75                  80

Glu Phe Ile Ser Lys Pro Ile Ile Ser Ile Asn Tyr Arg Ile
                85                  90
```

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide

<400> SEQUENCE: 3

```
Ser Ala Lys Thr Thr Pro Lys Leu Gly Gly
1               5                   10
```

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide

<400> SEQUENCE: 4

```
Arg Ala Asp Ala Ala Ala Ala Gly Gly Pro Gly Ser
1               5                   10
```

<210> SEQ ID NO 5
<211> LENGTH: 27
<212> TYPE: PRT
<213> ORGANISM: Artificial Sequence
<220> FEATURE:
<223> OTHER INFORMATION: Synthetic peptide

<400> SEQUENCE: 5

```
Arg Ala Asp Ala Ala Ala Ala Gly Gly Gly Gly Ser Gly Gly Gly Gly
1               5                   10                  15

Ser Gly Gly Gly Gly Ser Gly Gly Gly Gly Ser
            20                  25
```

<210> SEQ ID NO 6
<211> LENGTH: 26
<212> TYPE: PRT
<213> ORGANISM: Artificial Sequence
<220> FEATURE:
<223> OTHER INFORMATION: Synthetic peptide

<400> SEQUENCE: 6

```
Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25
```

<210> SEQ ID NO 7
<211> LENGTH: 17

```
<212> TYPE: PRT
<213> ORGANISM: Artificial Sequence
<220> FEATURE:
<223> OTHER INFORMATION: Synthetic peptide

<400> SEQUENCE: 7

Val Ser Gln Thr Ser Lys Leu Thr Arg Ala Glu Thr Val Phe Pro Asp
1               5                   10                  15

Val

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Ala Gly Asn Arg Val Arg Arg Ser Val Gly
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Thr Arg His Arg Gln Pro Arg Gly Trp Glu
1               5                   10

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10
atggccgttt ctgatgttcc gcgta                                     25

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11
gccgctggta cggtagttaa tcgag                                     25

<210> SEQ ID NO 12
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 12
atggggaaga tcactttta cgaggac                                    27

<210> SEQ ID NO 13
<211> LENGTH: 33
<212> TYPE: DNA
<213> ORGANISM: Artificial Sequence
```

<220> FEATURE:
<223> OTHER INFORMATION: Synthetic oligonucleotide

<400> SEQUENCE: 13
tcaataaaaa tccatcaccc gtcttaaaga acc                                33

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 14
atgagaggat cgcatcacca tcaccatcac                                    30

<210> SEQ ID NO 15
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 15
ttaattaagc ttttgcagga tttcagccag g                                  31

<210> SEQ ID NO 16
<211> LENGTH: 800
<212> TYPE: DNA
<213> ORGANISM: Artificial Sequence
<220> FEATURE:
<223> OTHER INFORMATION: Synthetic polynucleotide

<400> SEQUENCE: 16
agcgtttagc gcatcggcgg acgtcgtcga gcagaaattg atcagcgagg aggatctgat    60 ggccgttttct gatgttccgc gtaagctgga agttgttgct gcgacccga ctagcctgct   120 gatcagctgg gatgctcctt aatgaaggcc tctttattac cgtatcacgt acggtgaaac   180
cggtggtaac tccccggttc aggagttcac tgtacctggt tccaagtcta ctgctaccat   240
cagcggcctg aaaccgggtg ttgactatac catcactgta tacgctgtta cttaatgaag   300 gcctttatagc aagccaatct cgattaacta ccgtaccagc ggaggggag gttctggagg   360 cggtgggtct ggtggtggcg gctctggagg cggtggtagc ggaggcgag gttctgatta   420 caaggacgac gatgacaagc ttgctagcgc catggccgtt tctgatgttc gcgtaagct    480 ggaagttgtt gctgcgaccc cgactagcct gctgatcagc tgggatgctc cttaatgaag   540
gcctctttat taccgtatca cgtacggtga aaccggtggt aactccccgg ttcaggagtt   600
cactgtacct ggttccaagt ctactgctac catcagcggc ctgaaaccgg tgttgacta    660 taccatcact gtatacgctg ttacttaatg aaggcctat agcaagccaa tctcgattaa    720
ctaccgtacc agcggccgcg tcgacgggcg cgcccaattg atcgacccat tcgtttctga   780
atatcaaggc caatcgtctg                                               800

<210> SEQ ID NO 17
<211> LENGTH: 37
<212> TYPE: PRT
<213> ORGANISM: Artificial Sequence
<220> FEATURE:
<223> OTHER INFORMATION: Synthetic peptide

<400> SEQUENCE: 17

```
Glu Gln Lys Leu Ile Ser Glu Glu Asp Leu Met Ala Val Ser Asp Val
1               5                   10                  15

Pro Arg Lys Leu Glu Val Val Ala Ala Thr Pro Thr Ser Leu Leu Ile
            20                  25                  30

Ser Trp Asp Ala Pro
        35
```

<210> SEQ ID NO 18
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 18

```
Arg Pro Leu Tyr Tyr Arg Ile Thr Tyr Gly Glu Thr Gly Gly Asn Ser
1               5                   10                  15

Pro Val Gln Glu Phe Thr Val Pro Gly Ser Lys Ser Thr Ala Thr Ile
            20                  25                  30

Ser Gly Leu Lys Pro Gly Val Asp Tyr Thr Ile Thr Val Tyr Ala Val
        35                  40                  45

Thr Arg Pro Tyr Ser Lys Pro Ile Ser Ile Asn Tyr Arg Thr Ser Gly
    50                  55                  60

Gly Gly Gly Ser Gly Gly Gly Ser Gly Gly Gly Ser Gly Gly Ser Gly
65                  70                  75                  80

Gly Gly Ser Gly Gly Gly Ser Asp Tyr Lys Asp Asp Asp Lys
                85                  90                  95

Leu Ala Ser Ala Met Ala Val Ser Asp Val Pro Arg Lys Leu Glu Val
                100                 105                 110

Val Ala Ala Thr Pro Thr Ser Leu Leu Ile Ser Trp Asp Ala Pro
            115                 120                 125
```

<210> SEQ ID NO 19
<211> LENGTH: 49
<212> TYPE: PRT
<213> ORGANISM: Artificial sequence
<220> FEATURE:
<223> OTHER INFORMATION: Synthetic polypeptide

<400> SEQUENCE: 19

```
Arg Pro Leu Tyr Tyr Arg Ile Thr Tyr Gly Glu Thr Gly Gly Asn Ser
1               5                   10                  15

Pro Val Gln Glu Phe Thr Val Pro Gly Ser Lys Ser Thr Ala Thr Ile
            20                  25                  30

Ser Gly Leu Lys Pro Gly Val Asp Tyr Thr Ile Thr Val Tyr Ala Val
        35                  40                  45

Thr
```

<210> SEQ ID NO 20
<211> LENGTH: 14
<212> TYPE: PRT
<213> ORGANISM: Artificial sequence
<220> FEATURE:
<223> OTHER INFORMATION: Synthetic peptide

<400> SEQUENCE: 20

```
Arg Pro Tyr Ser Lys Pro Ile Ser Ile Asn Tyr Arg Thr Ser
1               5                   10
```